United States Patent
Sterrett et al.

(10) Patent No.: US 11,116,449 B2
(45) Date of Patent: Sep. 14, 2021

(54) CATHETER SHAFT WITH ELECTRICALLY-CONDUCTIVE TRACES

(71) Applicant: St. Jude Medical, Cardiology Division, Inc., St. Paul, MN (US)

(72) Inventors: Terry L. Sterrett, Huntington Beach, CA (US); Allyn Jensrud, Burnsville, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 495 days.

(21) Appl. No.: 15/114,763

(22) PCT Filed: Jan. 28, 2015

(86) PCT No.: PCT/US2015/013308
§ 371 (c)(1),
(2) Date: Jul. 27, 2016

(87) PCT Pub. No.: WO2015/116692
PCT Pub. Date: Aug. 6, 2015

(65) Prior Publication Data
US 2016/0338647 A1    Nov. 24, 2016

Related U.S. Application Data

(60) Provisional application No. 61/932,499, filed on Jan. 28, 2014.

(51) Int. Cl.
A61B 5/00 (2006.01)
A61B 18/14 (2006.01)
(Continued)

(52) U.S. Cl.
CPC ............ *A61B 5/6852* (2013.01); *A61B 5/287* (2021.01); *A61B 18/1492* (2013.01);
(Continued)

(58) Field of Classification Search
CPC . A61B 5/6852; A61B 5/0422; A61B 18/1492; A61N 1/056; A61M 25/0012
See application file for complete search history.

(56) References Cited

U.S. PATENT DOCUMENTS

| 4,476,872 A | 10/1984 | Perlin |
| 4,762,135 A | 8/1988 | van der Puije et al. |

(Continued)

FOREIGN PATENT DOCUMENTS

| EP | 0989384 A2 | 3/2000 |
| EP | 1772097 | 4/2007 |

(Continued)

OTHER PUBLICATIONS

"CathPrint AB", Technology Brochure—A New Catheter & Endoscopic Paradigm. Publication date unknown. CathPrint AB, Stockholm, Sweden.
(Continued)

*Primary Examiner* — Peter Dungba Vo
*Assistant Examiner* — Jeffrey T Carley
(74) *Attorney, Agent, or Firm* — Dykema Gossett PLLC

(57) ABSTRACT

Methods of manufacturing and assembling a catheter shaft may include depositing electrical traces on an interior surface of the shaft of the catheter, rather than using separate wires, forming a bore in a sensor, and electrically coupling the sensor to the trace through a bore in the sensor.

16 Claims, 11 Drawing Sheets

(51) Int. Cl.
  *A61N 1/05* (2006.01)
  *A61B 5/287* (2021.01)
  *A61B 17/00* (2006.01)
  *A61B 18/00* (2006.01)
  *A61M 25/00* (2006.01)
  *A61B 90/00* (2016.01)

(52) U.S. Cl.
  CPC .... *A61N 1/056* (2013.01); *A61B 2017/00526* (2013.01); *A61B 2018/00029* (2013.01); *A61B 2018/00577* (2013.01); *A61B 2018/00839* (2013.01); *A61B 2018/00875* (2013.01); *A61B 2090/065* (2016.02); *A61B 2218/002* (2013.01); *A61B 2562/227* (2013.01); *A61M 25/0012* (2013.01)

(56) References Cited

U.S. PATENT DOCUMENTS

| | | | |
|---|---|---|---|
| 5,016,646 A * | 5/1991 | Gotthardt | A61N 1/056 607/122 |
| 5,300,068 A | 4/1994 | Rosar et al. | |
| 5,343,860 A | 9/1994 | Metzger et al. | |
| 5,840,024 A | 11/1998 | Taniguchi et al. | |
| 5,840,031 A | 11/1998 | Crowley | |
| 5,964,705 A * | 10/1999 | Truwit | A61B 5/055 324/318 |
| 6,024,702 A * | 2/2000 | Iversen | A61B 5/0422 600/378 |
| 6,210,339 B1 | 4/2001 | Kiepen et al. | |
| 6,233,476 B1 | 5/2001 | Strommer et al. | |
| 6,357,447 B1 | 3/2002 | Swanson et al. | |
| 6,498,944 B1 | 12/2002 | Ben-Haim et al. | |
| 6,569,162 B2 | 5/2003 | He | |
| 6,571,125 B2 * | 5/2003 | Thompson | A61M 5/14276 604/20 |
| 6,690,963 B2 | 2/2004 | Ben Haim et al. | |
| 6,788,967 B2 | 9/2004 | Ben Haim et al. | |
| 7,197,354 B2 | 3/2007 | Sobe | |
| 7,229,437 B2 | 6/2007 | Johnson et al. | |
| 7,263,397 B2 | 8/2007 | Hauck et al. | |
| 7,304,373 B2 | 12/2007 | Taggart et al. | |
| 7,386,339 B2 | 6/2008 | Strommer et al. | |
| 7,536,218 B2 | 5/2009 | Govari et al. | |
| 7,625,617 B1 | 12/2009 | Anderson et al. | |
| 7,686,802 B2 | 3/2010 | Stevens-Wright | |
| 8,147,486 B2 | 4/2012 | Honour et al. | |
| 8,221,408 B2 | 7/2012 | Johnson et al. | |
| 8,295,902 B2 | 10/2012 | Salahieh et al. | |
| 8,467,844 B2 | 6/2013 | Rea et al. | |
| 2002/0080233 A1 | 6/2002 | Irion et al. | |
| 2003/0187347 A1 | 10/2003 | Nevo et al. | |
| 2003/0195406 A1 | 10/2003 | Jenkins et al. | |
| 2004/0260241 A1 * | 12/2004 | Yamamoto | A61N 1/056 604/117 |
| 2005/0038320 A1 * | 2/2005 | Hartwick | A61B 1/00071 600/109 |
| 2005/0060885 A1 | 3/2005 | Johnson et al. | |
| 2005/0065508 A1 | 3/2005 | Johnson et al. | |
| 2005/0085716 A1 | 4/2005 | Hamm et al. | |
| 2006/0091508 A1 | 5/2006 | Taggart et al. | |
| 2007/0060833 A1 | 3/2007 | Hauck | |
| 2007/0219551 A1 | 9/2007 | Honour et al. | |
| 2009/0143651 A1 * | 6/2009 | Kallback | A61B 5/02007 600/301 |
| 2009/0171274 A1 | 7/2009 | Harlev et al. | |
| 2009/0227885 A1 | 9/2009 | Lowery et al. | |
| 2009/0247942 A1 | 10/2009 | Kirschenman | |
| 2009/0247944 A1 | 10/2009 | Kirschenman et al. | |
| 2009/0247993 A1 | 10/2009 | Kirschenman et al. | |
| 2009/0248042 A1 | 10/2009 | Kirschenman et al. | |
| 2010/0022950 A1 | 1/2010 | Anderson et al. | |
| 2010/0094279 A1 | 4/2010 | Kauphusman et al. | |
| 2010/0228112 A1 | 9/2010 | von Malmborg | |
| 2010/0256558 A1 | 10/2010 | Olson et al. | |
| 2010/0262040 A1 | 10/2010 | von Malmborg | |
| 2010/0318019 A1 | 12/2010 | Nee et al. | |
| 2011/0015569 A1 | 1/2011 | Kirschenman et al. | |
| 2011/0034912 A1 * | 2/2011 | de Graff | H01L 27/14687 606/21 |
| 2011/0066029 A1 | 3/2011 | Lyu et al. | |
| 2012/0029504 A1 | 2/2012 | Afonso et al. | |
| 2012/0143298 A1 | 6/2012 | Just | |
| 2012/0172696 A1 * | 7/2012 | Kallback | A61B 5/0215 600/373 |
| 2012/0172761 A1 | 7/2012 | Meller et al. | |
| 2012/0172842 A1 | 7/2012 | Sela et al. | |
| 2013/0066193 A1 | 3/2013 | Olson et al. | |
| 2013/0066194 A1 | 3/2013 | Seter et al. | |
| 2013/0169272 A1 | 7/2013 | Eichler et al. | |
| 2013/0172715 A1 | 7/2013 | Just | |
| 2013/0184549 A1 | 7/2013 | Avitall et al. | |
| 2014/0005768 A1 | 1/2014 | Estes et al. | |
| 2014/0030122 A1 | 1/2014 | Ozaki et al. | |
| 2014/0088591 A1 | 3/2014 | Just | |
| 2014/0142409 A1 | 5/2014 | Garcia et al. | |
| 2014/0303452 A1 * | 10/2014 | Ghaffari | A61B 1/05 600/301 |

FOREIGN PATENT DOCUMENTS

| | | | |
|---|---|---|---|
| EP | 2208456 | 7/2010 | |
| EP | 2032201 | 4/2013 | |
| JP | 2088237732 A | 10/2008 | |
| JP | 2011200340 A | 10/2011 | |
| WO | 0232497 A1 | 4/2002 | |
| WO | 2007139479 | 12/2007 | |
| WO | 2009120982 | 10/2009 | |
| WO | 2011005165 | 1/2011 | |
| WO | WO 2011005165 A1 * | 1/2011 | ............ A61M 25/00 |
| WO | 2011031201 A1 | 3/2011 | |
| WO | 2010129661 A1 | 11/2011 | |
| WO | 2012177807 A1 | 12/2012 | |
| WO | 2013074036 | 5/2013 | |

OTHER PUBLICATIONS

"CathPrint AB", Technology Brochure—CathPrint Prefab Catheter. Publication date unknown. CathPrint AB, Stockholm, Sweden.
"CathPrint AB", Technology Brochure—CathPrint Simple Catheter. Publication date unknown. CathPrint AB, Stockholm, Sweden.
"CathPrint AB", Technology Brochure—CathPrint Integrated Composite Catheter. Publication date unknown. CathPrint AB, Stockholm, Sweden.

* cited by examiner

CATHETER SHAFT WITH ELECTRICALLY-CONDUCTIVE TRACES

CROSS-REFERENCE TO RELATED APPLICATION

This application claims the benefit of U.S. provisional application No. 61/932,499, filed 28 Jan. 2014, now pending.

BACKGROUND a. Technical Field

The instant disclosure relates to elongate medical devices, including the electrical infrastructure of elongate medical devices.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like, and/or other sensors.

Catheters with electrodes and other sensors requiring electrical connections generally include one or more wires for at least a portion of the electrical infrastructure between the sensor and the handle of the catheter (e.g., for connection to one or more external systems). For example, in some processes, one or more electrical wires are soldered to each sensor at the distal end of the catheter and are later coupled with a connector in the handle at the proximal end of the catheter. Assembling such a catheter shaft may be complicated. First, the numerous soldering operations may require a high degree of manual skill. Second, a bundle of electrical wires must be managed throughout the assembly process without damaging the wires, the sensors, and/or the solder joints, and without confusing which wire or wires connects with which sensor. Finally, the wire bundle must be routed through the final shaft, occupying space within the shaft and requiring intricate handling of the wire bundle.

Including a wire bundle in the electrical infrastructure of a catheter may additionally cause operational issues with the catheter, which may lead to the catheter being scrapped during manufacture. For example, one or more wires in the bundle may become displaced (e.g., as a result of the bending and twisting inherent in operation of a catheter), which may lead to an open circuit, lumen obstruction, and/or an open circuit within the catheter.

The foregoing discussion is intended only to illustrate the present field and should not be taken as a disavowal of claim scope.

BRIEF SUMMARY

Manufacturing and assembly methods that improve on known catheter manufacturing and assembly techniques may generally include printing electrical traces on an interior surface of the shaft of the catheter, rather than using separate wires, and electrically coupling sensors to respective trace through a bore in each sensor.

For example, one exemplary embodiment of a method of manufacturing a shaft for an elongate medical device, the shaft defining a longitudinal axis, may include depositing an electrically-conductive trace on an interior structure and placing a sensor radially-outward of the interior structure. The method may further include forming a bore in the sensor and electrically coupling the sensor with the electrically-conductive trace through the bore.

An exemplary method of providing an electrical infrastructure for a sensor on an elongate medical device may include depositing an electrically-conductive trace on a surface of a shaft of the elongate medical device and physically coupling the sensor with the shaft. The method may further include forming a bore in the sensor and electrically coupling the sensor with the trace through the bore.

An exemplary elongate medical device shaft may comprise an inner tube defining a longitudinal axis, an electrically-conductive trace disposed on an outer surface of the inner tube, and an outer, electrically-insulative tube. The elongate medical device shaft may further include a sensor disposed radially outward of a portion of the electrically-conductive trace, the sensor defining a bore, and an electrically conductive element disposed in the bore, the electrically-conductive element electrically coupling the sensor with the electrically-conductive trace.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
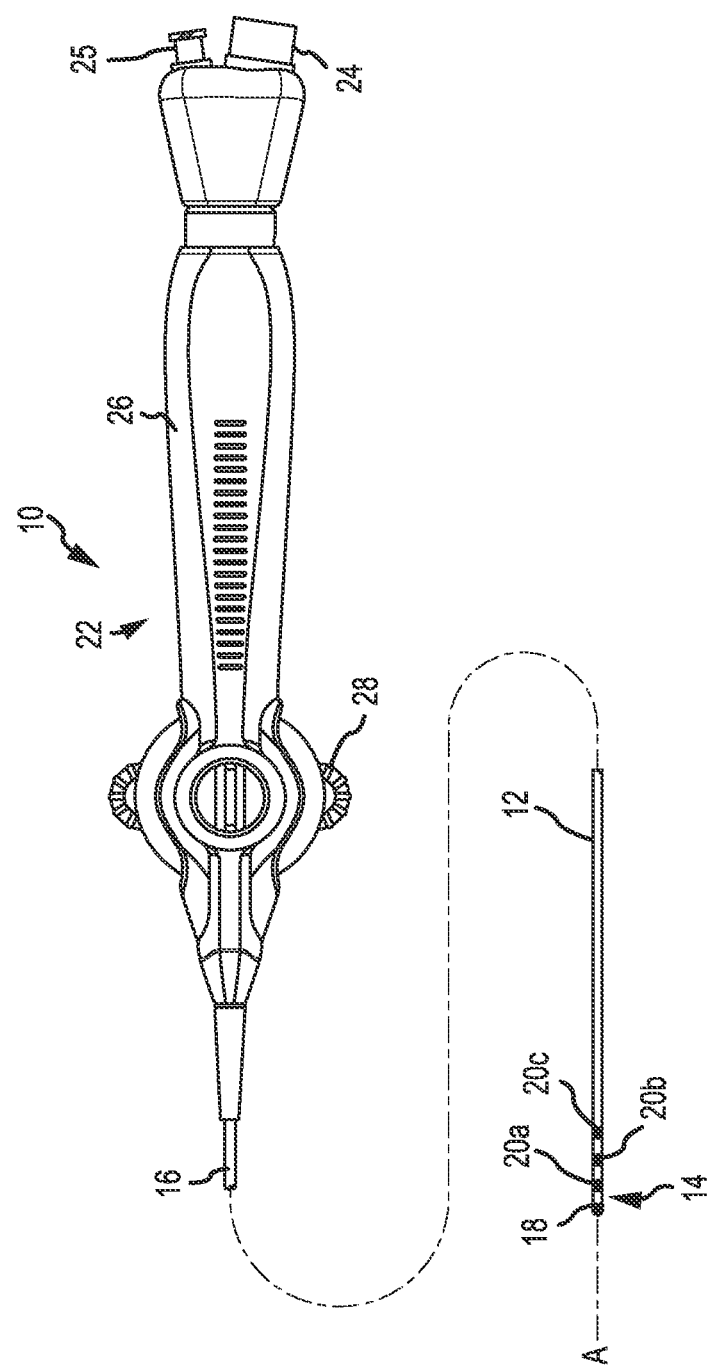
FIG. 1 is a plan view of an exemplary elongate medical device.

Referring now to the figures, in which like numerals indicate the same or similar elements in the various views, FIG. 1 is a plan view of an exemplary elongate medical device 10. The elongate medical device 10 may be a catheter, introducer, or other elongate medical device type. The elongate medical device 10 will be referred to herein as a catheter for ease of description (i.e., catheter 10). It should be understood, though, that the elongate medical device is not limited to a catheter.

The catheter 10 may include an elongate tubular shaft 12 defining a longitudinal axis A and having a distal end portion 14 and a proximal end portion 16, a tip electrode 18, a number of ring electrodes 20a, 20b, 20c (which may be referred to collectively as the ring electrodes 20 or individually as a ring electrode 20), and a handle 22 coupled with the catheter shaft 12. The handle 22 may include one or more electromechanical connectors 24 configured to allow the catheter 10, and the electrodes 18, 20 thereof, in particular, to be coupled with components or subsystems of, for example, an electrophysiology (EP) laboratory system. Such components or subsystems may comprise, for example and without limitation, a visualization, navigation, and/or mapping system, an EP monitoring and recording system (e.g., for monitoring and/or recording electrocardiograms (EGM), cardiac signals, etc.), a tissue contact sensing system, an ablation system, a cardiac stimulation system (i.e., EP stimulator), and the like. An exemplary system is shown in U.S. patent application publication no. 2012/0029504, which is hereby incorporated by reference in its entirety as though fully set forth herein.

The catheter 10 may further comprise one or more fluid connectors 25 configured to provide the catheter 10, and particularly the shaft 12, with connectivity between one or more fluid lumen(s) in the shaft 12 and external systems. The fluid connector 25 may thus be fluidly coupled with one or more fluid lumens in the shaft 12 and/or handle 22 and may be configured for connection with a source or destination of such fluids such as, for example only, a gravity feed or pump for irrigation fluids.

In addition to and/or instead of one or more electrodes 18, 20, the catheter 10 may be equipped with one or more additional types of sensors. For example, the catheter 10 may be equipped with one or more coil sensors, temperature sensors, pressure sensors, and/or other sensors. Additionally, some or all of the steps, methods, and procedures described and/or illustrated herein related to the manufacturing, assembly, and use of electrodes 18, 20 on the catheter 10 may also apply to other types of sensors disposed on or in the catheter 10.

The handle 22 may be disposed at the proximal end portion 16 of the shaft 12. The handle 22 may provide a location for a clinician to hold the catheter 10 and may further provide means for steering or guiding the shaft 12 within the body of a patient.

The handle 22 may comprise a housing 26. The housing 26 may be of a unitary construction or may be constructed of a plurality of pieces that are configured to be assembled together. In a multi-piece embodiment, the housing 26 may be coupled together in any number of ways known in the art, such as, for example, by press fit or interference coupling techniques, by complementary interlocking members, by conventional fasteners or adhesives, or any other techniques known in the art.

Within the housing 26, one or more wires may be provided to electrically couple the electromechanical connector 24 with the electrical infrastructure of the shaft 12. For example, in an embodiment, one wire may be provided for each electrical trace on a surface of the shaft, as shown and described in detail below. A wire in the housing 26 may be soldered to an electrical trace on one end, for example, and soldered or otherwise electrically coupled to the electromechanical connector 24 within the housing 26 on the other end.

In an exemplary embodiment, the catheter 10 may further comprise a deflection mechanism 28 associated with the handle 22 of the catheter 10. The deflection mechanism 28 may be coupled with a pull assembly (not shown) disposed at or in the distal end portion 14 of the shaft 12. The combination of the deflection mechanism 28 and the pull assembly provides a means by which a user or physician can effect movement (e.g., deflection) of the distal end portion 14 in one or more directions, and therefore, allows the physician to steer the catheter shaft 12.

Figure 2:
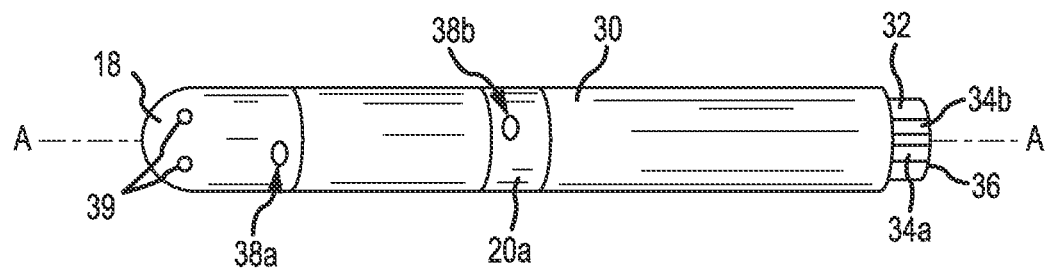
FIG. 2 is an isometric view of an exemplary embodiment of a distal end portion of an elongate medical device.

FIG. 2 is an isometric view of an embodiment of the distal end portion 14 of the catheter 10, with a portion of an outer tube 30 of the shaft 12 cut away to expose an inner tube 32. The inner tube 32 may extend within the outer tube 30, and a first electrically-conductive trace 34a and a second electrically-conductive trace 34b may be disposed on an outer surface 36 of the inner tube 32. The distal end portion 14 may include, as noted above, a tip electrode 18 and one or more ring electrodes 20 (one such ring electrode 20a is shown in FIG. 2). The tip electrode 18 may define a first bore 38a (i.e., via), and the ring electrode may define a second bore 38b (i.e., via). Bores 38a and 38b and other bores shown and/or described herein may be referred to collectively as the bores 38 or individually as the bore 38. Each bore 38 may extend, substantially orthogonal to the axis A of the shaft 12, from an exterior surface of the electrode 18, 20 to a portion of a respective one of the traces 34. Thus, the first bore 38a may extend from an exterior surface of the tip electrode 18, through a portion of the body of the electrode 18 to a portion of a first trace 34a, and the second bore 38b may extend from the exterior surface of the ring electrode 20a to a portion of a second trace 34b. Thus, the first bore 38a may be axially coincident with a portion of the first trace 34a, and the second bore 38b may be axially coincident with a portion of the second trace 34b.

The first bore 38a may be filled with an element (e.g., a material) that electrically couples the tip electrode 18 with the first trace 34a, and the second bore 38b may also be filled with an element (e.g., a material) that electrically couples the band electrode 20a with the second trace 34b. For example, in an embodiment, each bore 38 may be filled with an electrically-conductive adhesive. Such an electrically-conductive adhesive may include, for example only, silver-filled polyurethane, epoxy, and/or silicone adhesive.

The tip electrode 18 may further include one or more irrigation ports 39, in an embodiment. Irrigation fluid may be provided from a system disposed at the proximal end of the catheter (e.g., a gravity feed or pump, as noted above) and may flow through the irrigation ports 39 in order to, for example only, cool the tip electrode. Additional details regarding irrigated electrodes may be found, for example, in U.S. Pat. Nos. 8,517,999 and 8,187,267, both of which are hereby incorporated by reference in their entireties.

In an embodiment, the inner tube 32 may comprise some or all of a fluid lumen for the catheter 10. The fluid lumen may be configured to carry one or more fluids (e.g., irrigation fluid) between the handle of the finished device and the distal tip of the finished device. Fluid may flow through the inner tube 32 to the irrigation ports 39, in an embodiment.

Referring to FIGS. 1 and 2, each of the electrically-conductive traces 34 may extend from the distal end portion 14 of the shaft 12 (e.g., from a point axially-coincident with a respective one of the electrodes 18, 20) to the proximal end portion 16 of the shaft 12, in an embodiment. Each trace 34 may extend over substantially the entire length of the shaft 12, in an embodiment. For example, each trace 34 may extend over 90% or more of the length of the catheter shaft 12. In an embodiment, one or more of the traces 34 may include one or more interruptions and/or discontinuities. For example but without limitation, a distal portion of a trace 34 may extend from the distal end portion 14 of the shaft 12, be electrically coupled with a distal end of a flex circuit, such as a flex circuit as illustrated and described in U.S. patent application publication no. 2012/0172842, which is hereby incorporated by reference in its entirety as though fully set forth herein, and a proximal portion of the trace 34 may be electrically coupled with a proximal end of the flex circuit and may continue extending proximally to the proximal end portion 16 of the shaft 12.

FIGS. 3A-14 illustrate several stages of buildup in a method of manufacturing and assembling an embodiment of the catheter shaft 12 illustrated in FIGS. 1 and 2. More particularly, FIGS. 3A-9 illustrate an exemplary method of depositing one or more electrically-conductive traces 34 on an inner tube 32 of a catheter shaft 12, and FIGS. 10A-14 illustrate further steps in an exemplary method of manufacturing and assembling a catheter shaft 12 that may include the inner tube 32 with electrically-conductive traces 34. It should be understood that the steps and methods shown and described herein are exemplary in nature only. Steps may be added, altered, and/or omitted without departing from the spirit and scope of the instant disclosure.

Figure 3A:
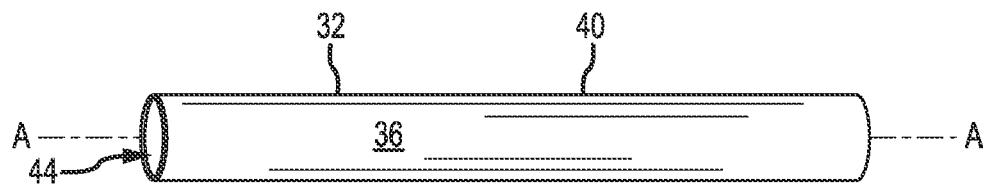
FIGS. 3A-9 are isometric views of an inner tube that may form a part of an elongate medical device shaft illustrating various stages in a first exemplary embodiment of a method of depositing electrically-conductive traces on the inner tube.
Figure 3B:
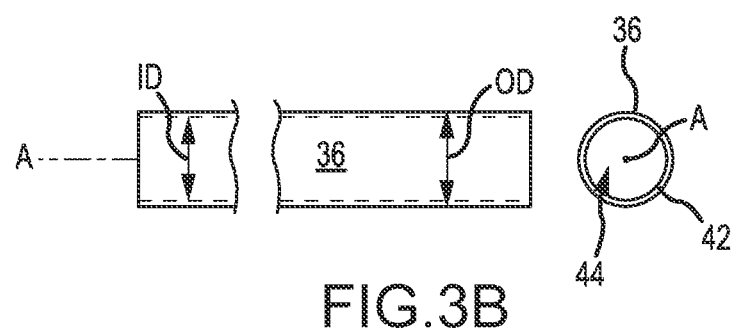

Referring to FIGS. 3A-9, a method of depositing one or more electrically-conductive traces 34 on an inner tube 32 may begin with providing an inner tube 32. FIG. 3A is an isometric view of an intermediate portion 40 of the inner tube 32, and FIG. 3B includes a side view of the intermediate portion 40 and an end view of the inner tube 32. The inner tube 32 may have an inner diameter and an outer diameter defining a wall 42, and may define an inner lumen 44.

In an embodiment, the inner tube 32 may have an inner diameter of about 0.032 inches, an outer diameter of about 0.0365 inches, a wall thickness of about 0.0045 inches, and a length of about 60 inches. The inner tube 32 may be an extruded polymer, in an embodiment. Alternatively, the inner tube may be formed from a flat substrate, which is rolled and bonded to form a tube. The rolling and bonding may happen before or after other process steps of the various methods illustrated and/or described herein.

The inner tube 32 may comprise, for example but without limitation, a polymer, such as polyimide. Additionally or alternatively, the inner tube 32 may be or may include polyethylene-naphthalate (PEN), such as a PEN film. For example, the inner tube 32 may be or may include a PEN film commercially available under the trade name Teonex®, such as Teonex® Q65FA or Teonex® Q83. Additionally or alternatively, the inner tube 32 may be or may include polyethylene terephthalate (PET), such as a PET film. For example, the inner tube 32 may be or may include a PET film commercially available under the trade name Melinex®, such as Melinex® ST506 or Melinex® ST504.

Additionally or alternatively, the inner tube 32 may comprise another material having material characteristics suitable for one or more of heightened processing temperatures temperatures (e.g., capable of withstanding temperatures involved in melt processing further layers of a catheter shaft), for the materials deposition methods and steps described or referenced herein, and for a minimum thickness.

Additionally, the materials comprising the inner tube 32 may be appropriate for safely transmitting fluid (i.e., in a biologically-compatible manner) through the lumen 44 of the inner tube 32. Thus, the lumen 44 may act as a fluid lumen in the finished device for, e.g., the flow of irrigation fluid to the tip of the device.

Figure 4:
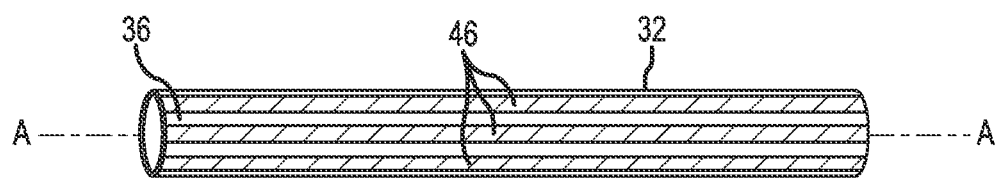

Referring to FIG. 4, one or more masks 46 may be placed on the exterior surface 36 of the inner tube 32. The masks 46 may comprise materials and processes known in the art such as, for example, those offered commercially by Enthone, Inc. of West Haven, Conn.

The masks 46 may be placed on the exterior surface 36 of the inner tube 32 to define the line width (i.e., width of a given trace 34), spacing between traces 34, and pattern requirements of a particular application. In an embodiment, the line width of an individual trace 34 may be between about 25 µm and about 100 µm. The masks 46 may be placed on every portion of the outer surface 36 of the inner tube 32 where an electrically-conductive trace 34 is not desired (i.e., negative masking), in an embodiment. Alternatively, the masks 46 may be placed on the portions of the outer surface 36 of the inner tube 32 where an electrically-conductive trace 34 is desired (i.e., positive masking), in an embodiment. The remainder of the description herein will be with respect to an embodiment employing negative masking, but it should be understood that this is for ease of description only, and is not limiting.

Figure 5:
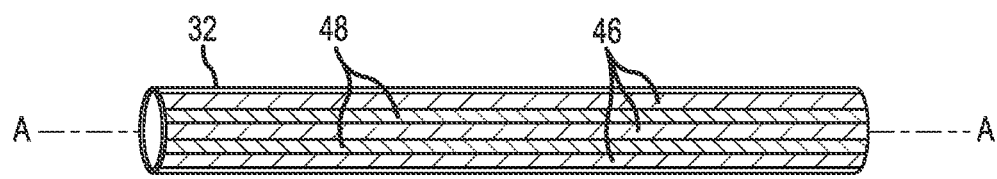

Referring to FIG. 5, a seed layer 48 may then be deposited on the exposed (i.e., non-masked) portions of the outer surface 36 of the inner tube 32. The seed layer 48 may comprise, for example and without limitation, copper or another suitable metal. The seed layer 48 may be deposited through, for example, chemical vapor deposition (CVD), physical vapor deposition (PVD), electrografting, and/or known "wet" methods of deposition. Electrografting may be performed, for example, according to a technique described in Frederic Raynal (2012), "Integration of Electrografted Layers for the Metallization of Deep Through Silicon Vias," Electroplating, Prof. Darwin Sebayang (Ed.), ISBN: 978-953-51-0471-1, which is hereby incorporated by reference in its entirety as though fully set forth herein.

In addition to a seed layer 48, a tiecoat layer may be deposited. The tiecoat layer may be deposited in substantially the same manner as the seed layer 48, in an embodiment (e.g., according to chemical vapor deposition (CVD), physical vapor deposition (PVD), etc.). The tiecoat layer may be deposited before the seed layer 48. The tiecoat material may comprise a chromium-based or nickel-based alloy, in an embodiment. The tiecoat layer may improve the adhesion of electrically-conductive materials to the inner tube 32.

Figure 6:
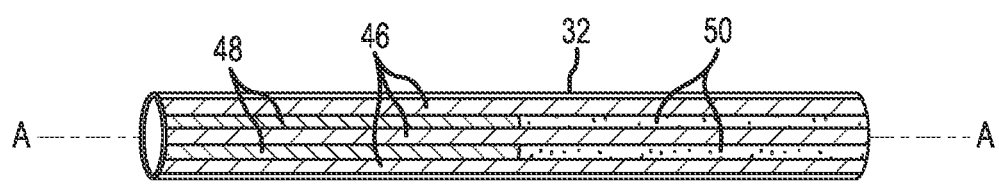
Figure 7:
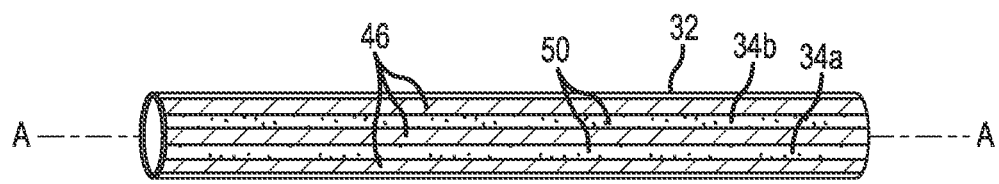

A conductive layer 50 may then be deposited on top of the seed layer 48, as shown in FIGS. 6 (illustrating partial conductive layer 50 deposition) and 7 (illustrating completed conductive layer 50 deposition). The conductive layer 50 may comprise a conductive metal such as, for example and without limitation, copper, nickel, and/or gold. The conductive layer may be deposited through electroplating, electroless deposition, CVD, and/or PVD, for example.

Figure 8:
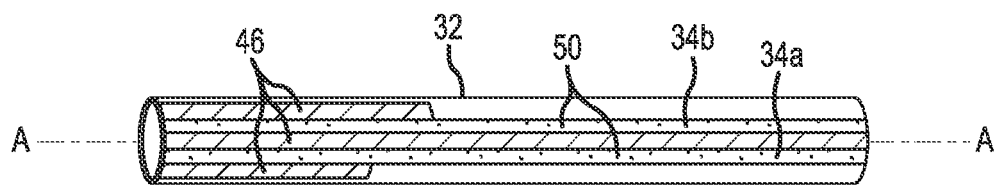
Figure 9:

The mask layer 46 may be removed, as illustrated in FIGS. 8 (illustrating partial mask removal) and 9 (illustrating complete mask removal). The masks 46 may be removed using conventional mask removal materials (e.g., solvents) and processes, which materials and processes may be selected according to the materials used for the masks 46.

In some embodiments, the mask layer 46 may be left intact on the inner tube 32. For example, the mask layer 46 may be left intact where positive masking is employed. The mask layer 46 may also be left intact (i.e., in an embodiment employing negative masking) to serve as a dielectric between adjacent traces 34. In particular, the mask layer 46 may be left intact as a dielectric layer in embodiments in which the space between traces 34 in relatively small.

In an additional process step, a coating layer may be deposited over the traces 34, remaining masks 46, and/or exposed portions of the outer surface 36 of the inner tube 32. For example, a coating layer comprising polymer, such as, for example only, that sold under the trade name PARYLENE HT, available from Specialty Coating Systems, Inc. of Indianapolis, Ind. may be deposited. The coating layer may be deposited through CVD and/or PVD, in an embodiment. The coating layer may be provided, for example, as a dielectric and/or to prevent physical damage to the traces 34 during further manufacturing and assembly steps of a catheter shaft 12 including the inner tube 32, as well as during use of the finished catheter shaft 12.

After the mask layer 46 is removed (or with the mask layer 46 still intact), the result may be an inner tube 32 on which one or more electrically-conductive traces 34 are disposed. The steps illustrated in FIGS. 3A-9 may be used to deposit electrically conductive traces 34 in a desired pattern. Deposited traces 34 may include, for example and without limitation, longitudinal straight lines, circumferential contact pads, serpentine patterns, spiral patterns, etc. Such patterns may be deposited to provide an electrical infrastructure through which one or more sensors (such as the electrodes 18, 20, see FIGS. 1 and 2) may be electrically connected to external systems (e.g., through an electromechanical connector in the handle disposed at the proximal end of the shaft).

Deposited traces 34 may also be used to form sensors themselves. For example, deposited traces 34 may be used to form sensors such as, for example only, GPS antennas, coils for use in electromagnetic positioning systems, etc.

As an alternative to the process steps illustrated in FIGS. 4-9, electrically-conductive traces 34 may be deposited on the inner tube 32 by printing. Printed ink traces 34 may comprise copper or silver ink, in an embodiment. Traces 34 may be printed with equipment and processes known in the art such as, for example, equipment available from Optomec, Inc. of Albuquerque, N. Mex.

In an alternative process, electrically-conductive traces 34 may be printed on a non-cylindrical inner structure, substantially according to the steps illustrated and described herein. The non-cylindrical inner structure may then, in an embodiment, be formed into a tube or other shape with adhesive and/or other fastening means. If formed into a tube or tube-like structure, such inner layer may thereafter serve as an inner tube 32 for later manufacturing steps, assembly steps, and uses described herein. For example, traces 34 may be printed as illustrated and/or described in co-pending U.S. provisional patent application No. 61/932,386, filed Jan. 28, 2014, which is hereby incorporated by reference in its entirety as though fully set forth herein.

In an exemplary embodiment in which the inner tube 32 is formed from polyimide, the polyimide may be pretreated in a plasma pretreatment process before deposition of electrically-conductive and other materials. The plasma pretreatment may improve adhesion of the deposited materials relative to a non-pretreated polyimide.

FIGS. 10A-14 illustrate further steps in a method of manufacturing and assembling a catheter shaft 12 that may include the inner tube 32 with electrically-conductive traces 34. Various embodiments of a distal end portion 52a, 52b, 52c of various embodiments 32a, 32b, 32c of the inner tube 32 are shown in FIGS. 10A-12.

Figure 10A:
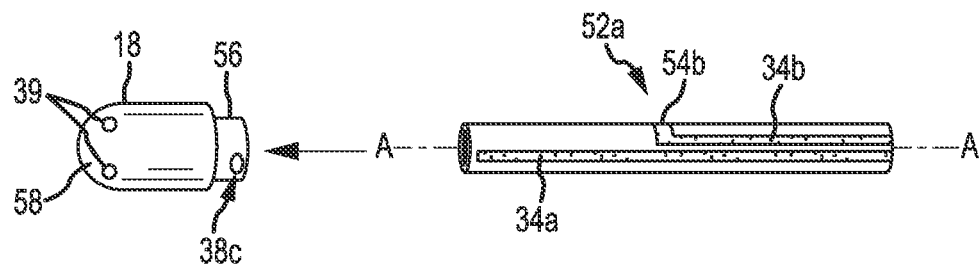
FIGS. 10A-14 are isometric views of an elongate medical device shaft assembly illustrating various stages in a method of assembling the elongate medical device shaft.
Figure 10B:
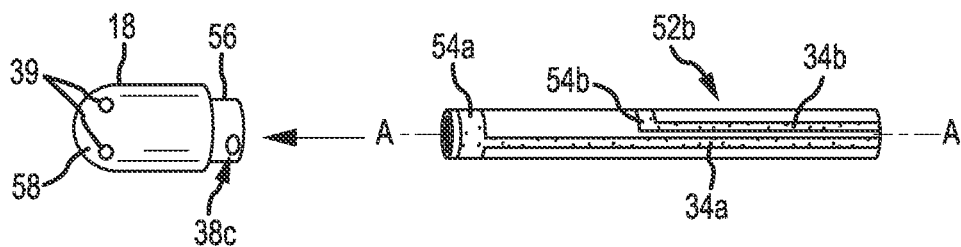

As shown in FIGS. 10A and 10B, a tip electrode 18 may be provided. As shown in FIG. 10A, the tip electrode 18a may be configured to be electrically coupled with the distal tip of a longitudinal trace 34a, in an embodiment. Additionally or alternatively, as shown in FIG. 10B, the inner tube distal end portion 52b may include, and the tip electrode 18b may be configured to be electrically coupled with, a circumferential bonding pad 54a. The circumferential bonding pad 54a may be deposited according to the steps and methods described above in conjunction with FIGS. 3A-9. The circumferential bonding pad 54a may include a circumferential dimension that is larger than the longitudinal dimension of the bonding pad 54a. In an embodiment, the bonding pad 54a may extend around the entire circumference of the inner tube distal end portion 52b. Alternatively, a bonding pad 54 may extend around less than the entire circumference of the inner tube distal end portion 52a, 52b, 52c. For example, as shown in both FIGS. 10A and 10B, a bonding pad 54b may be provided that does not extend around the entire circumference of the inner tube distal end portion 52a, 52b. It should be noted that the bonding pads 54a, 54b, and similar structures may be described herein collectively as the bonding pads 54, or individually as a bonding pad 54.

The tip electrode 18a, 18b may include a neck portion 56 and a body portion 58, in an embodiment. The neck portion 56 may include a bore 38c, in an embodiment. The bore 38c may be formed by laser drilling, mechanical drilling, and/or another bore-formation technique. The bore 38c may extend into the body portion 58 of the tip electrode 18, substantially orthogonal to the longitudinal axis of the final catheter shaft. In other embodiments, the neck portion 56 of the tip electrode 18 may lack a bore 38c.

Figure 11A:
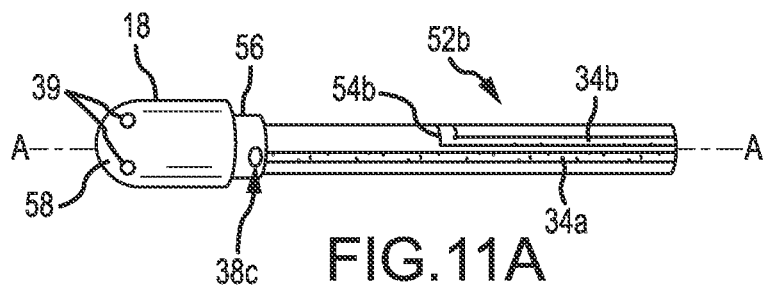
Figure 11B:
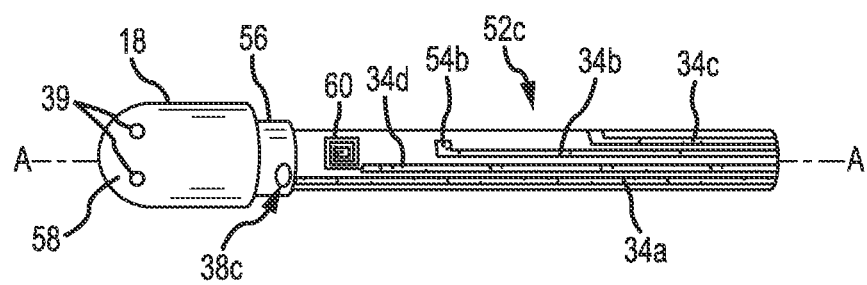

The inner tube distal end portion 52a, 52b, 52c may be inserted into a cavity in the proximal end of the tip electrode 18, in an embodiment, as shown in FIGS. 11A and 11B. The cavity may extend through the neck portion 56 and at least partially into the body portion 58, in an embodiment. The inner tube distal end portion 52a, 52b, 52c may be inserted such that a portion of an electrically-conductive trace 34 is circumferentially coincident with the bore 38c in the neck portion 56.

The inner tube 32 may be rigidly coupled (e.g., bonded) with the tip electrode 18 using an adhesive, in an embodiment. For example, the inner tube 32 may be rigidly coupled with the tip electrode 18 with an electrically-insulative adhesive. Alternatively, the inner tube 32 may be rigidly coupled with the tip electrode 18 with an electrically-conductive adhesive. In an embodiment, such adhesive may provide an electrical coupling between one or more traces 34 on the inner tube 32 and the tip electrode 18.

Following coupling of the tip electrode 18 with the inner tube 32, the bore 38c in the neck portion 56 of the tip electrode 18 may be cleaned out (e.g., to remove electrically non-conductive adhesive and/or other debris). In an embodiment, the bore 38c may be cleaned out through laser drilling. In particular, the bore 38c may be cleaned out if an electrically-insulative adhesive is used to couple the tip electrode 18 with the inner tube 32.

The bore in the neck portion of the tip electrode 18, if provided, may be filled with an element that electrically couples the electrically-conductive trace 34a with the tip electrode 18. For example, in an embodiment, the bore 38c may be filled with an electrically-conductive adhesive.

As shown in FIG. 11B, and as noted above, in an embodiment, electrically-conductive traces 34 may be deposited on the inner tube 32 so as to form a sensor. For example only, electrically-conductive traces may be deposited in a spiral formation to form an antenna 60 that may be used, for example only, to receive GPS signals.

Figure 12:
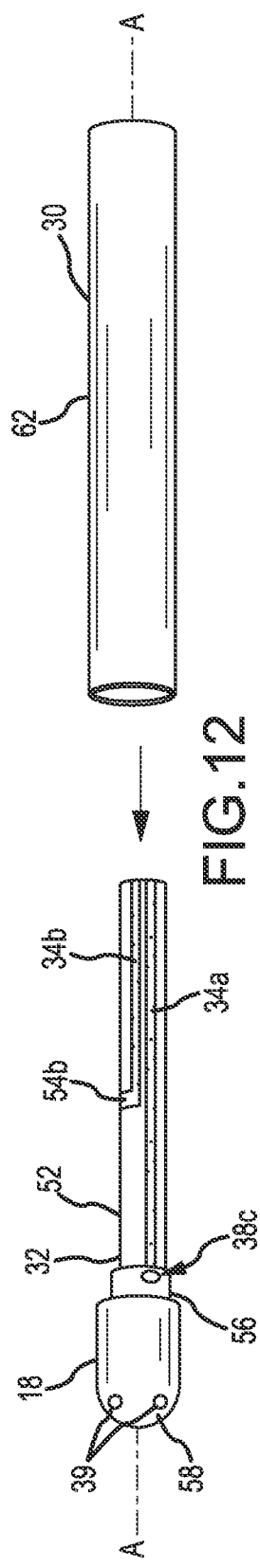
Figure 13:
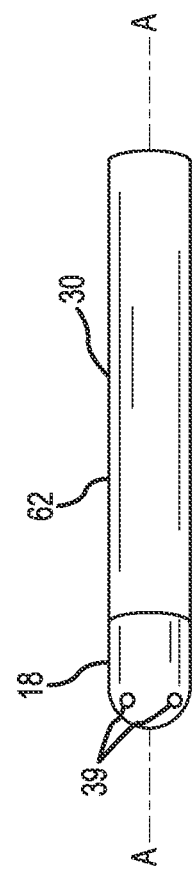
Figure 14:
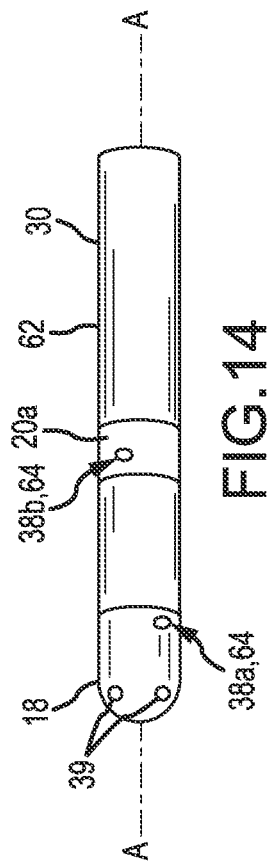

Referring to FIG. 12, an outer tube 30 may be provided (FIGS. 12-14 show a distal end portion 62 of the outer tube 30). The outer tube 30 may comprise a polymer such as, for example and without limitation, polyether block amide (PEBA). The outer tube 30 may be pre-formed (e.g., before being placed over the inner tube 32) to a desired shape and dimensions (e.g., desired inner diameter, outer diameter, and length). The outer tube 30 may be pre-formed by extrusion or melt processing on a separate mandrel, for example. Alternatively, the outer tube 30 may be melt-processed on the inner tube 32 (and/or on another layer of the catheter shaft 12) to obtain desired dimensions. The outer tube 30 may have an outer diameter that is substantially the same as the outer diameter of the tip electrode 18, in an embodiment.

Referring to FIG. 13, the outer tube 30 may be placed over the inner tube 32 and the neck portion 56 of the tip electrode 18. The outer tube 30 may be rigidly coupled (e.g., bonded) to the tip electrode 18, in an embodiment. For example, the inner surface of the outer tube 30 may be rigidly coupled to the outer surface of the neck portion 56 of the tip electrode 18 with electrically-insulative adhesive or electrically-conductive adhesive.

Referring to FIG. 14, one or more ring electrodes 20 may be placed over the outer tube 30 (one such ring electrode 20a is shown in FIG. 14). Each ring electrode 20 may be placed to be axially-coincident with a portion of a respective electrically-conductive trace 34 on the inner tube 32. For example, each ring electrode 20 may be placed such that a portion of each ring electrode 20 is axially coincident with a bonding pad 54. Each ring electrode 20 may be rigidly coupled with the outer tube 30 such as, for example only, with adhesive.

One or more bores 38 may be made in each electrode 18, 20, in an embodiment. Each bore 38 may be made by, for example only, laser drilling and/or mechanical drilling. Each bore 38 may be substantially orthogonal to the longitudinal axis A of the shaft, and may extend from an outer surface of the electrode 18, 20, through the electrode 18, 20, and, for the ring electrodes 20, through any portion of the outer tube 30 that is radially inward of the electrode 20. Each bore 38 may thus provide a hole from the outer surface of the electrode 18, 20 to a portion of an electrically-conductive trace 34. A bore 38 may be circular, in an embodiment, or may have some other shape, in another embodiment.

Through a respective bore 38, an element may be provided to electrically couple each electrode 18, 20 with a respective electrically-conductive trace 34. In an embodiment, for example, each bore 38 may be filled with electrically-conductive adhesive 64.

In an embodiment, one or more of the bores 38 may be formed in the electrodes 18, 20 and/or the outer tube 30 before assembly of the inner tube 32, tip electrode 18, outer tube 30, and ring electrodes 20. Accordingly, in an embodiment, a part of the assembly process may involve placing the inner tube 32, tip electrode 18, outer tube 30, and/or ring electrodes 20 to line up bores 38 and traces 34 with each other.

The catheter 10 may operate with a variety of catheter systems such as visualization systems, mapping systems, and navigation support and positioning systems (i.e., for determining a position and orientation (P&O) of a flexible elongate member or other medical device). One such system is illustrated in FIG. 15.

Figure 15:
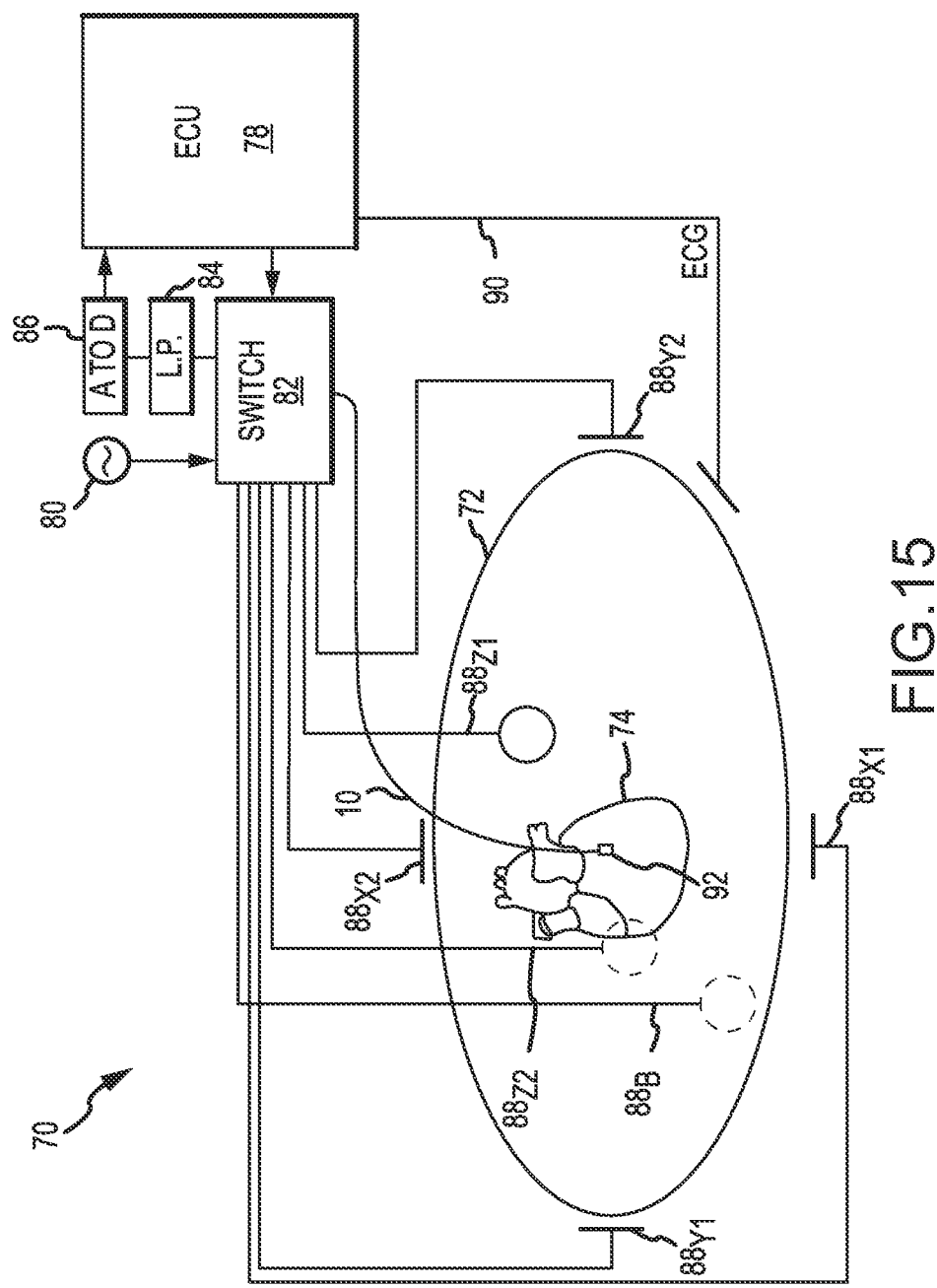
FIG. 15 is a schematic and diagrammatic view of an embodiment of a medical device mapping and navigation system.
Figure 16A:
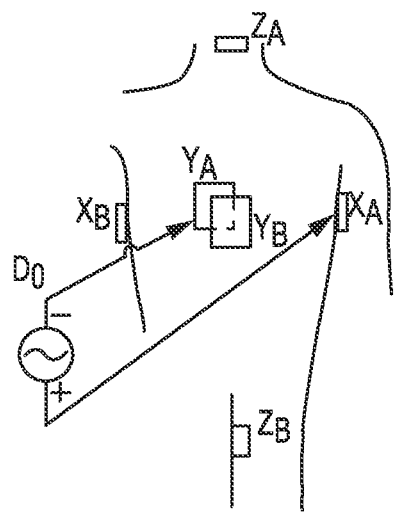
FIGS. 16A-16D are diagrammatic views of exemplary dipoles created using the mapping and navigation system of FIG. 15.
Figure 16B:
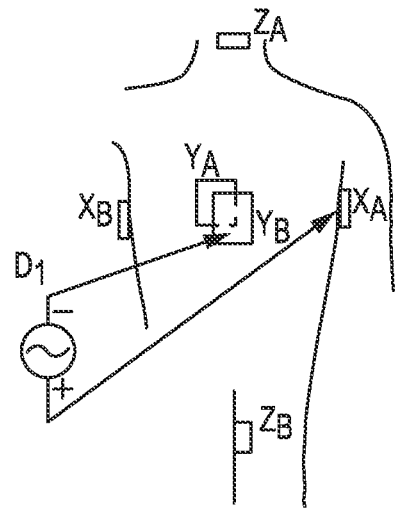
Figure 16C:
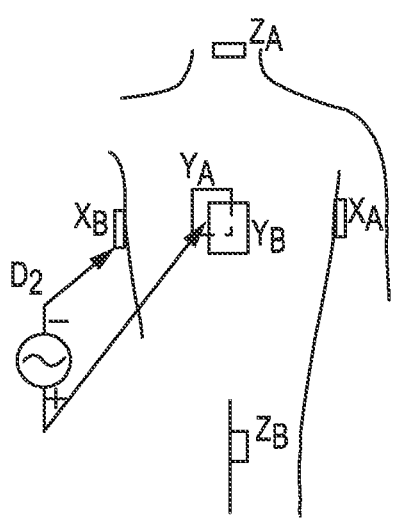
Figure 16D:
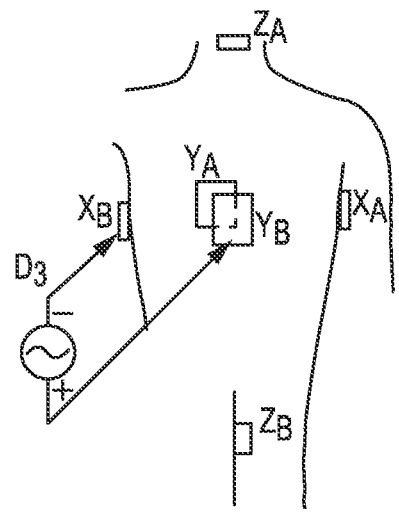

FIG. 15 is a schematic and diagrammatic view of an embodiment of a medical device mapping and navigation system 70. The system 70 is coupled with a catheter 10 that can be guided to and disposed in a portion of a body 72, such as a heart 74. The catheter 10 can include one or more sensors (which may be one or more of the electrodes 18, 20, see FIGS. 1, 2 and 10A-14) for, e.g., collecting electrophysiology data, applying ablation energy, and/or determining a location of the catheter 10 within the body 72. The system 70 may include, at least in part, an electronic control unit (ECU) 78, a signal generator 80, a switch 82, a low-pass filter 84, an analog-to-digital (A-to-D) converter 86, a plurality of body surface electrode patches $88_B$, $88_{X1}$, $88_{X2}$, $88_{Y1}$, $88_{Y2}$, $88_{Z1}$, $88_{Z2}$, and electrocardiogram (ECG) patches 90.

The system 70 is provided for visualization, mapping, and/or navigation of internal body structures and may be referred to herein as "the navigation system." The navigation system 70 may comprise an electric field-based system, such as, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. Nos. 7,263,397 and 7,885,707, both hereby incorporated by reference in their entireties as though fully set forth herein. In other exemplary embodiments, the navigation system 70 may comprise systems other than electric field-based systems. For example, the navigation system 70 may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 70 may comprise a magnetic field-based system based on the MediGuide™ technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the navigation system 70 may comprise a combination electric field-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the navigation system 70 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 70 will be described hereinafter as comprising an electric field-based system, such as, for example, the EnSite™ NavX™ system identified above.

The catheter 10 and sensors may be provided for a variety of diagnostic and therapeutic purposes including, for example, electrophysiological studies, pacing, cardiac mapping, and ablation. In an embodiment, the catheter 10 can be an ablation catheter, mapping catheter, or other elongate medical device. The number, shape, orientation, and purpose of the sensors may vary in accordance with the purpose of the catheter 10. In an embodiment, at least one sensor can be an electrode 18, 20. For purposes of illustration, the description below will be with respect to an embodiment in which the sensors comprise one or more electrodes 18, 20, but the disclosure is not limited to such an embodiment.

With the exception of the patch electrode $88_B$ called a "belly patch," the patch electrodes 88 are provided to generate electrical signals used, for example, in determining the position and orientation of the catheter 10 and in the guidance thereof In one embodiment, the patch electrodes 88 are placed generally orthogonally on the surface of the body and are used to create axes-specific electric fields within the body. For instance, in one exemplary embodiment, patch electrodes $88_{X1}$, $88_{X2}$ may be placed along a first (x) axis. Patch electrodes $88_{Y1}$, $88_{Y2}$ may be placed along a second (y) axis, and patch electrodes $88_{Z1}$, $88_{Z2}$ may be placed along a third (z) axis. Each of the patch electrodes 88 may be coupled to the multiplex switch 82. In an exemplary embodiment, the ECU 78 may be configured, through appropriate software, to provide control signals to the multiplex switch 82 to thereby sequentially couple pairs of electrodes 88 to the signal generator 80. Excitation of each pair of electrodes 88 (e.g., in either orthogonal or non-orthogonal pairs) generates an electrical field within the patient's body 72 and within an area of interest such as the heart 74. Voltage levels at non-excited electrodes 88, which are referenced to the belly patch $88_B$, are filtered by the low-pass filter 84 and converted by the A-to-D converter 86 and provided to the ECU 78 for use as reference values.

As noted above, one or more electrodes 18, 20 may be mounted in or on the catheter 10. In an exemplary embodiment, at least one of the electrodes 18, 20 comprises a positioning electrode 92 and is configured to be electrically coupled to the ECU 78. With a positioning electrode 92 electrically coupled to the ECU 78, the positioning electrode 92 may be placed within electrical fields created in the body 72 (e.g., within the heart 74) by exciting the patch electrodes 88. The positioning electrode 92 experiences voltages that are dependent on the position of the positioning electrode 92 relative to the locations of the patch electrodes 88. Voltage measurement comparisons made between the positioning electrode 92 and the patch electrodes 88 may be used to determine the position of the positioning electrode 92 relative to the heart 74 or other tissue. Movement of the positioning electrode 92 proximate a tissue (e.g., within a chamber of the heart 74) may produce information regarding the geometry of the tissue. This information may be used, for example, to generate models and maps of anatomical structures. Such maps and models may reflect a particular state of the anatomical structure such as, for example, the shape of the heart at a particular point in the cardiac cycle. Position information determined according to measurements made with the positioning electrode 92 may thus be associated with a particular portion of the cardiac cycle based on readings from the ECG patches 90. Information received from the positioning electrode 92 can also be used to display on a display device, the location and orientation of the positioning electrode 92 and/or a portion of the catheter 10 relative to the heart 74 or other tissue. Accordingly, among other things, the ECU 78 of the navigation system 70 may provide a means for generating display signals used to control a display and the creation of a graphical user interface (GUI) on the display.

The ECU 78 may comprise a programmable microprocessor or microcontroller, or may comprise an application specific integrated circuit (ASIC). The ECU 78 may include a an input/output (I/O) interface through which the ECU 78 may receive a plurality of input signals including, for example, signals generated by patch electrodes 88 and the positioning electrode 92 (among others), and generate a plurality of output signals including, for example, those used to control a display and other user interface components. The ECU 78 may be configured to perform various functions with appropriate programming instructions or code (i.e., software). Accordingly, the ECU 78 can be programmed with one or more computer programs encoded on a computer-readable storage medium for performing functionality described herein.

FIGS. 16A-16D show a plurality of exemplary non-orthogonal dipoles, designated $D_0$, $D_1$, $D_2$ and $D_3$. Referring to FIGS. 15 and 16A-16D, for any desired axis, the potentials measured across an intra-cardiac positioning electrode 92 resulting from a predetermined set of drive (source-sink) configurations may be combined algebraically to yield the same effective potential as would be obtained by simply driving a uniform current along the orthogonal axes. Any two of the patch electrodes 88 may be selected as a dipole source and drain with respect to a ground reference, e.g., belly patch $88_B$, while the unexcited body surface electrodes 88 measure voltage with respect to the ground reference $88_B$. The positioning electrode 92 placed in the heart 74 is also exposed to the field from a current pulse and is measured with respect to ground, e.g., the belly patch $88_B$. In practice, a catheter 10 or multiple catheters 10 within the heart 74 may contain multiple positioning electrodes 92 and each positioning electrode potential may be measured separately.

Data sets from each of the patch electrodes 88 and the positioning electrode 92 may be used to determine the location of the positioning electrode 92 within the heart 74. After the voltage measurements are made, a different pair of surface electrodes 88 is excited by the signal generator 80 and the voltage measurement process of the remaining patch electrodes 88 and positioning electrode 92 takes place. The sequence occurs rapidly, e.g., on the order of 100 times per second, in an embodiment. To a first approximation, the voltage on the positioning electrode 92 within the heart 74 bears a linear relationship with position between the patch electrodes 88 that establish the field within the heart 74, as more fully described in U.S. Pat. No. 7,263,397 referred to above.

In summary, FIG. 15 shows an exemplary navigation system 70 that employs seven body surface electrodes (patches) 88, which may be used for injecting current and sensing resultant voltages. Current may be driven between two patches 88 at any time; some of those driven currents are illustrated in FIGS. 16A-16D. Measurements may be performed between a non-driven patch 88 and, for example, the belly patch 88$_B$ as a ground reference. A patch bio-impedance, also referred to as a "patch impedance" may be computed according to the following equation:

$$BioZ[c \to d][e] = \frac{V_e}{I_{c \to d}} \quad (1)$$

where $V_e$ is the voltage measured on patch e and $I_{c \to d}$ is a known constant current driven between patches c and d, where patches c, d, and e may be any of the patch electrodes 88. The position of a positioning electrode 92 may be determined by driving current between different sets of body patches 88 and measuring one or more patch impedances along with the voltage on the positioning electrode 92. In one embodiment, time division multiplexing may be used to drive and measure all quantities of interest. Position determining procedures are described in more detail in U.S. Pat. Nos. 7,263,397 and 7,885,707 referred to above, as well as other references.

FIGS. 17-20B are various views of an inner tube that may form a part of an elongate medical device shaft illustrating various stages in a second exemplary embodiment of a method of depositing electrically-conductive traces 34 on the inner tube 32. The second method illustrated in FIGS. 17-20B may be an alternative to the process illustrated in and described with respect to FIGS. 3A-9, in an embodiment. As noted below, however, the second method may incorporate one or more steps of the first method, in an embodiment.

The second method may generally involve applying electrically-conductive traces 34 on a stretched substrate, then releasing the tension on the substrate, resulting in a larger surface area for the traces 34 in the direction of tension application than the underlying substrate. As a result, the traces 34 may be better able to withstand stress resulting from bending of a device in which the substrate and traces 34 are incorporated, such as an elongate medical device. The second method will be described below with respect to an embodiment in which the substrate is the inner tube 32. It should be understood, however, that the second method may also find use with embodiments in which the substrate is a structure other than the inner tube 32. And, as noted above, in an embodiment, the inner tube 32 may be formed from a flat substrate rolled and bonded so as to form a tube; in a version of the second method, the steps illustrated and described herein may be performed with such a substrate in flat or rolled form.

Figure 17:
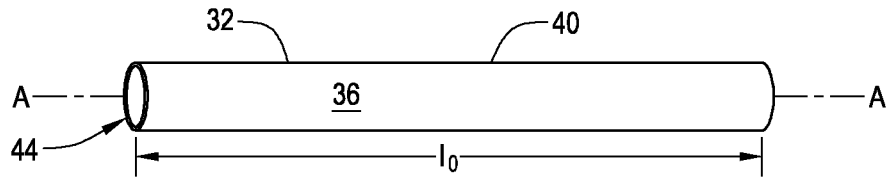
FIGS. 17-20B are various views of an inner tube that may form a part of an elongate medical device shaft illustrating various stages in a second exemplary embodiment of a method of depositing electrically-conductive traces on the inner tube.
Figure 18:
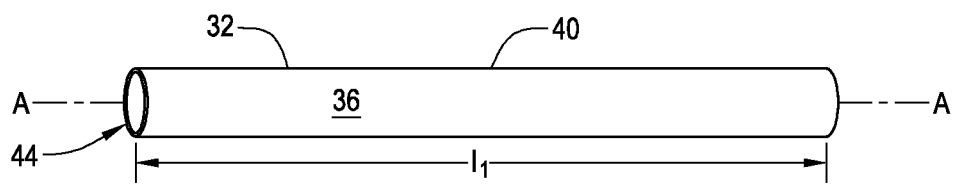

FIG. 17 is an isometric view of an intermediate portion 40 of the inner tube 32. Referring to FIGS. 17 and 18, the inner tube 32 may be stretched. For example, in an embodiment, the inner tube 32 may be stretched along the axis A. In an embodiment, the inner tube 32 may be stretched along multiple axes. The ratio of the amount of stretching along multiple axes may be determined according to Poisson's ratio, in an embodiment, and may therefore address the multi-axial stresses on the inner tube 32 resulting from deflection along a single axis that are described by Poisson's ratio. The inner tube 32, or a portion thereof (e.g., the intermediate portion 40), may be stretched from its static length $l_0$ (illustrated in FIG. 17) to a stretched length $l_1$ (illustrated in FIG. 18). The inner tube 32 may be stretched, for example, by securing the ends of the inner tube 32 with clamps and moving the clamps relative to each other.

The inner tube 32, or a portion thereof, may be stretched to at least 140% of its static (i.e., steady, non-stretched) length and less than 200% of its steady, non-stretched length, in an embodiment. That is, $l_1$ may be between 40% and 100% greater than $l_0$, in an embodiment. The amount of stretching (i.e., the difference between $l_1$ and $l_0$) may depend on, for example, the materials comprising the inner tube 32 and the desired deflection tolerance of the inner tube 32. For example, the greater the amount of intended deflection of the inner tube 32 (and, thus, the greater the amount of bending over the length of the inner tube 32), the more the inner tube 32 may be stretched (i.e., the greater the difference between $l_1$ and $l_0$). Further, the greater the elasticity of the inner tube 32, the more the inner tube 32 may be stretched.

Figure 19:
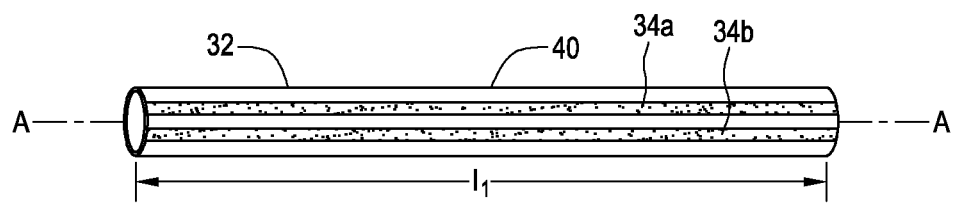

FIG. 19 is an isometric view of the inner tube intermediate portion 40 having electrically-conductive traces 34 disposed on the outer surface 36 of the inner tube 32. Two such traces 34a, 34b are illustrated in FIG. 19, but any number of traces 34 may be provided. The electrically-conductive traces 34 may be applied to the inner tube 32 while the inner tube is stretched (i.e., while axial tension is applied to the inner tube 32). The electrically conductive traces 34 may be applied to the inner tube 32 according to any of a number of methodologies. For example, in an embodiment, the electrically-conductive traces 34 may be printed on the inner tube 32 by using a print head under control of a processing device.

Figure 20A:
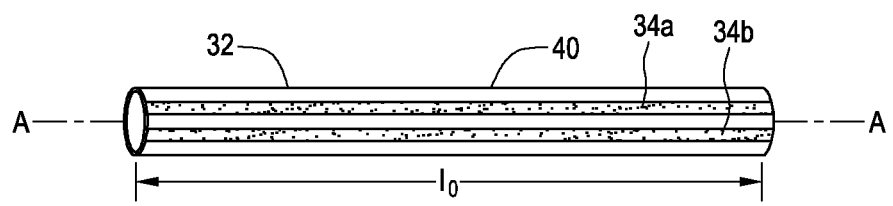

Following application of the electrically-conductive traces 34 to the inner tube 32, the tension may be released from the inner tube 32 to allow the inner tube 32 to return to its original, non-stretched length $l_0$. FIG. 20A is an isometric view of the inner tube intermediate portion 40 returned to its original, non-stretched length $l_0$, and FIG. 20B is an up-close side view of a portion of the inner tube intermediate portion returned to its original, non-stretched length $l_0$.

Figure 20B:

As illustrated in FIG. 20B, when the tension is released from the inner tube 32, the electrically-conductive traces 34 (one trace 34a is illustrated in FIG. 20B) may have axially-compressive tension applied by virtue of the attachment of the electrically-conductive traces 34 to the inner tube 32 as the inner tube 32 shortens in length. The compressive tension may cause the electrically-conductive traces 34 to "bunch," to partially separate from the inner tube, or to otherwise form a structure other than a flat trace as it would under a lack of tension, in an embodiment. An exemplary "bunching" of the trace 34a is illustrated in an exaggerated fashion in FIG. 20B. As a result, the electrically-conductive traces 34 may be better able to absorb axial stresses from bending of the inner tube 32 during operation of a device in which the inner tube 32 is used, such as an elongate medical device.

FIGS. 21-24 are isometric views of an inner tube 32 that may form a part of an elongate medical device shaft illustrating various stages in a third exemplary embodiment of a method of depositing electrically-conductive traces 34 on the inner tube 32. The steps illustrated in FIGS. 21-24 may be an alternative to the first method illustrated in and described with respect to FIGS. 3A-9 or the second method illustrated in and described with respect to FIGS 17-20B, in an embodiment.

Figure 21:
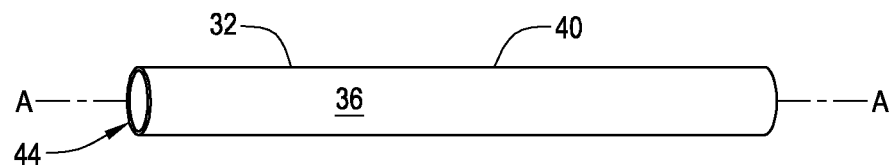
FIGS. 21-24 are isometric views of an inner tube that may form a part of an elongate medical device shaft illustrating various stages in a third exemplary embodiment of a method of depositing electrically-conductive traces on the inner tube.

Referring to FIG. 21, the method may begin with providing the inner tube 32 with the outer surface 36 exposed. FIG. 21 and subsequent figures illustrate an intermediate portion 40 of the inner tube 32.

Figure 22:
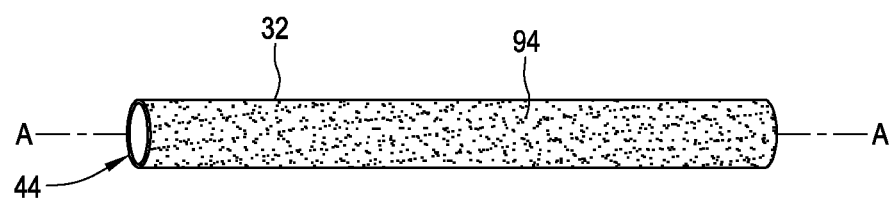

As shown in FIG. 22, a portion of the outer surface 36 of the inner tube 32 may be coated with a layer of electrically-conductive material 94. The electrically-conductive material 94 may be or may include, for example, copper, gold, silver, or some other material. The entire circumference of a given longitudinal section of the inner tube 32 may be coated, in an embodiment. Further, the entire circumference of the entire length of the inner tube may be coated, in an embodiment. The inner tube 32 may be coated with the layer of electrically-conductive material 94 according to any appropriate methodology. For example, chemical vapor deposition (CVD), physical vapor deposition (PVD), electrochemical deposition (ECD), or some other technique normally associate with semiconductor fabrication may be used.

Figure 23:
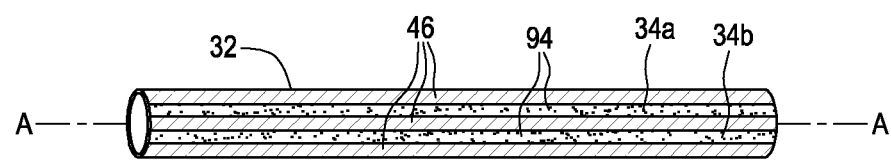
Figure 24:
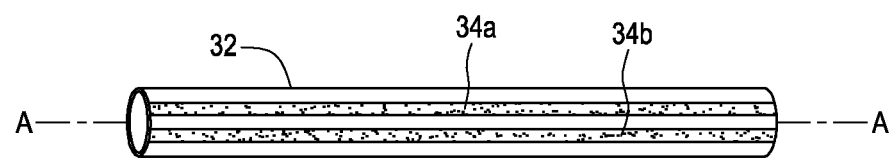

Referring to FIG. 23, portions of the layer of electrically-conductive material may be patterned (e.g., masked, exposed, developed, and etched, as generally known in semiconductor fabrication) to remove portions of the electrically-conductive material. As part of this procedure, as illustrated in FIG. 23, one or more masks 46 may be applied over the electrically-conductive layer 94. Portions of the layer of electrically-conductive material 94 may be removed to leave a desired pattern of electrically-conductive material. For example, one or more traces 34 may remain following patterning. FIG. 24 illustrates the inner tube 32 following patterning, with a two electrically-conductive traces 34a, 34b remaining.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of manufacturing a shaft for an elongate medical device, the shaft defining a longitudinal axis, the method comprising:
   applying axial tension to an interior structure;
   depositing an electrically-conductive trace on the interior structure after applying axial tension;
   releasing said axial tension after depositing the electrically-conductive trace;
   placing an electrically-insulative tube over the interior structure;
   placing a sensor radially-outward of the electrically-insulative tube and the interior structure, wherein the sensor is a band electrode;
   forming a constant diameter bore hole in the sensor and in the electrically-insulative tube, the bore hole extending orthogonal relative to the longitudinal axis; and
   electrically coupling the sensor with the electrically-conductive trace through the bore by filling the bore with an electrically-conductive adhesive.

2. The method of claim 1, wherein the interior structure comprises an inner tube.

3. The method of claim 1, further comprising depositing a circumferential contact pad on the interior structure, wherein a portion of the bore is longitudinally coincident with the contact pad.

4. The method of claim 1, wherein depositing the electrically-conductive trace comprises one or more of electroplating, electrografting, chemical-vapor deposition, and printing electrically-conductive ink.

5. The method of claim 1, wherein depositing the electrically-conductive trace comprises:
   coating an entire circumference of a longitudinal section of said interior structure with a layer of electrically-conductive material; and
   patterning the layer of electrically-conductive material to remove material not included in the trace.

6. A method of manufacturing a shaft for an elongate medical device, the shaft defining a longitudinal axis, the method comprising:
   depositing an electrically-conductive trace on an interior structure;
   placing an electrically-insulative tube over the interior structure;
   placing a sensor radially-outward of the interior structure and said electrically-insulative tube, wherein the sensor is a rounded tip electrode;
   forming a constant diameter bore in the sensor and the electrically-insulative tube; and
   electrically coupling the sensor with the electrically-conductive trace through the bore;
   wherein depositing the electrically-conductive trace comprises:
      coating an entire circumference of a longitudinal section of said interior structure with a layer of electrically-conductive material;
      patterning the layer of electrically-conductive material to remove material not included in the trace; and
      physically coupling the tip electrode with the interior structure via an electrically-conductive adhesive.

7. The method of claim 6, wherein electrically coupling the sensor with the electrically-conductive trace comprises filling the bore with the electrically-conductive adhesive.

8. The method of claim 6, wherein the interior structure comprises an inner tube.

9. A method of manufacturing a shaft for an elongate medical device, the shaft defining a longitudinal axis, the method comprising:
applying axial tension to an interior structure;
depositing an electrically-conductive trace on the interior structure after applying axial tension to the interior structure;
placing an electrically-insulative tube over the interior structure;
placing a sensor radially-outward of the interior structure and the electrically-insulative tube;
forming a constant diameter bore in the sensor and the electrically insulative tube;
electrically coupling the sensor with the electrically-conductive trace through the bore by filling the bore with an electrically-conductive adhesive; and
releasing said axial tension after depositing the electrically-conductive trace;
wherein depositing the electrically-conductive trace comprises:
coating an entire circumference of a longitudinal section of said interior structure with a layer of electrically-conductive material; and
patterning the layer of electrically-conductive material to remove material not included in the trace.

10. The method of claim 9, wherein the interior structure comprises an inner tube.

11. The method of claim 9, wherein the sensor is a band electrode.

12. The method of claim 9, wherein the sensor is a rounded tip electrode, further comprising physically coupling the tip electrode with the interior structure.

13. The method of claim 12, wherein physically coupling the tip electrode with the interior structure comprises physically coupling the tip electrode with the interior structure with the electrically-conductive adhesive.

14. The method of claim 1, wherein the bore hole is not a circumferentially extending cut in the electrically-insulative tube.

15. The method of claim 1, wherein the electrically-conductive adhesive does not radially extend beyond the bore hole in the sensor relative to a longitudinal axis defined by the bore hole.

16. The method of claim 1, wherein the step of forming the bore hole in the sensor and the electrically-insulative tube is a single operation; and
wherein the single operation is a drilling operation through both the sensor and the electrically-insulative tube.

* * * * *